(12) United States Patent
Barth et al.

(10) Patent No.: US 8,350,852 B2
(45) Date of Patent: Jan. 8, 2013

(54) DEVICE AND METHOD FOR RECONSTRUCTION AND VISUALIZATION OF PROJECTION DATA

(75) Inventors: Karl Barth, Hoechstadt (DE); Wolfgang Haerer, Erlangen (DE); Thomas Mertelmeier, Erlangen (DE); Karl Wiesent, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 601 days.

(21) Appl. No.: 12/581,986

(22) Filed: Oct. 20, 2009

(65) Prior Publication Data

US 2010/0097378 A1    Apr. 22, 2010

(30) Foreign Application Priority Data

Oct. 22, 2008  (DE) .......................... 10 2008 052 690

(51) Int. Cl.
*G06T 15/00*        (2011.01)
(52) U.S. Cl. ........ 345/420; 345/419; 345/422; 345/428; 382/128; 382/131; 382/285; 378/46

(58) Field of Classification Search .................. 345/419, 345/420, 422, 428; 382/128, 131, 285; 378/46
See application file for complete search history.

(56) References Cited

U.S. PATENT DOCUMENTS

| 7,310,436 | B2 | 12/2007 | Li et al. | |
|---|---|---|---|---|
| 7,522,755 | B2* | 4/2009 | Li et al. | ........................ 382/128 |
| 7,558,366 | B2 | 7/2009 | Barth et al. | |

OTHER PUBLICATIONS

"Filtered Backprojection for Modifying the Impulse Response of Circular Tomosynthesis," Stevens et al., Med. Phys., vol. 28, No. 3 (2001), pp. 372-380.
"Ultra-Fast 3D Filtered Backprojection on Commodity Graphics hardware," Xu et al., IEEE International Symposium on Biomedical Imaging (2004) pp. 1-4.

* cited by examiner

*Primary Examiner* — Phu K Nguyen
(74) *Attorney, Agent, or Firm* — Schiff Hardin LLP

(57) ABSTRACT

In a device and associated method for reconstruction and visualization of projection data, projection data are stored per slice and are subjected to an image reconstruction procedure in parallel within arbitrary slice planes in a processor-controlled filtering process that is executed n times, wherein volume data that are created can already be made available (loaded) for a direct visualization.

14 Claims, 8 Drawing Sheets

DEVICE AND METHOD FOR RECONSTRUCTION AND VISUALIZATION OF PROJECTION DATA

BACKGROUND OF THE INVENTION

1. Field of the Invention

The present invention concerns computerized devices and methods for operating on projection data to reconstruct an image therefrom, and for displaying (visualizing) the reconstructed image.

2. Description of the Prior Art

A reconstruction of volume data based on projection data leads (for example in medical image processing or in materials testing) to more detailed spatial insights and enables a substantiated diagnosis. For example, the projection data can be acquired by means of x-rays, electrically (for example with impedance), optically or acoustically (for example with sonography).

A method of slice image generation of the type known as tomosynthesis can be used in cases in which computed tomography is not available. Such a method is described in, for example, the DE 102006012407. Perceptible delays in the visualization of volume data result due to the large number of digital projection data sets that must be processed.

SUMMARY OF THE INVENTION

An object of the present invention is to provide a device and an associated method for reconstruction and visualization of projection data.

The above object is achieved in accordance with the present invention by a device and an associated method for reconstruction and visualization of projection data, wherein the projection data are stored on a slice-by-slice basis and are subjected to an image reconstruction procedure in parallel within arbitrary slice planes in a processor-controlled filtering process, that is executed n times. Volume data that are created in this manner can already be made available (loaded) for a direct visualization before the entire image reconstruction procedure is completed for all of the projection data.

The invention has the advantage that only one processing unit and one memory are required for both the processing of the raw projection data and the visualization of the projection data.

The invention also has the advantage that both the pre-processing and the reconstruction-related filtering and the reconstruction ensue in 3D blocks.

The invention has the further advantage that the required calculations in the 3D blocks ensue through closed transformation of complete 2D planes.

The invention also has the advantage that individual slices can already be visualized for diagnosis before completely finishing a tomosynthesis acquisition cycle.

The invention has the advantage that a 3D reconstruction can be conducted in real time.

DESCRIPTION OF THE PREFERRED EMBODIMENTS

Figure 1:
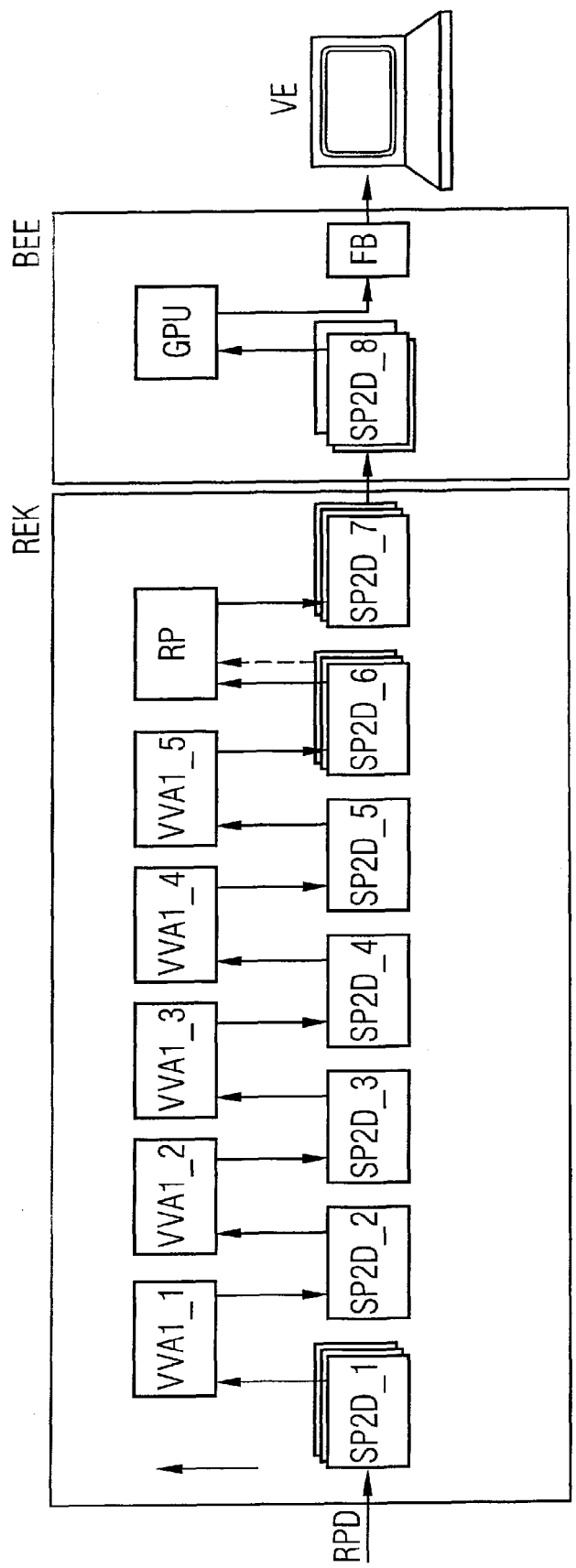
FIG. 1 is a block diagram of an image reconstruction and visualization procedure according to the prior art.

Relevant prior art with regard to the present object of the present invention is described in U.S. Pat. No. 7,310,436. FIG. 1 illustrates how a system is schematically designed according to this prior art. The depicted processing units are formed by, among other things, a reconstruction unit REK and an image generation unit BEE. On the input side, the reconstruction unit REK is supplied with data (data set) of a volume projection V that can also be designated as raw projection data RPD. The raw projection data RPD are obtained, for example, directly from a detector unit D of a C-arm, or are transferred therefrom to the reconstruction unit REK. The first through k-th pre-processing units $VVA1\_i$, $i=I \ldots k$, the back-projection unit RP and the memories $SP2D\_j$, $j=I \ldots m$ in the reconstruction unit REK are components of the reconstruction unit REK. The data processing of the detected raw projection data RPD ensues in the pre-processing units $VVA1\_i$ and the back-projection unit RP with associated first memory units $SP2D\_j$. The raw projection data RPD of n x-ray exposures are first stored in a first memory unit $SP2D\_1$. A value scaling, physical correction, subtraction and an equalization are implemented in the first pre-processing unit $VVA1\_1$. A rotation in the image plane for general non-linear tomosynthesis is implemented in the second pre-processing unit $VVA1\_2$. A projection correction in the image plane is implemented in the third pre-processing unit $VVA1\_3$. A reconstruction-related filtering is implemented in the fourth pre-processing unit $VVA1\_4$. A reversal of the effect of the second processing unit $VVA1\_2$ is implemented in the fifth pre-processing unit $VVA1\_5$. A known back-projection algorithm that results in the generation of 3D data is executed in the back-projection unit RP. The processing units in the reconstruction unit REK sequentially process the image data. The data processing ensues per pixel (i.e., on a pixel-by-pixel basis and thus in two-dimensional space) in the reconstruction unit REK and in the image generation unit BEE. Each of the n exposures is processed in the processing units $VVA1\_1$ through $VVA1\_5$ and RP with caching in the provided memories after each unit. Even given sequential processing of one exposure after another, memory capacity in the amount of the complete exposure stack of the n exposures must be provided at least for $SP2D\_1$, $SP2D\_6$ and $SP2D\_7$. In addition to a graphics processor GPU, a memory unit $SP2D\_8$ is arranged in the image generation unit BEE. The slice data calculated by the reconstruction unit REK are stored in the memory unit $SP2D\_8$. Slice images or section images of the exposed subject O are displayed according to the specifications of the viewer with the aid of the graphics processor GPU in the visualization unit BEE.

This arrangement entails the disadvantage that the memory requirement is considerable and a visualization of the reconstructed volume data in real time cannot be achieved.

Figure 2:
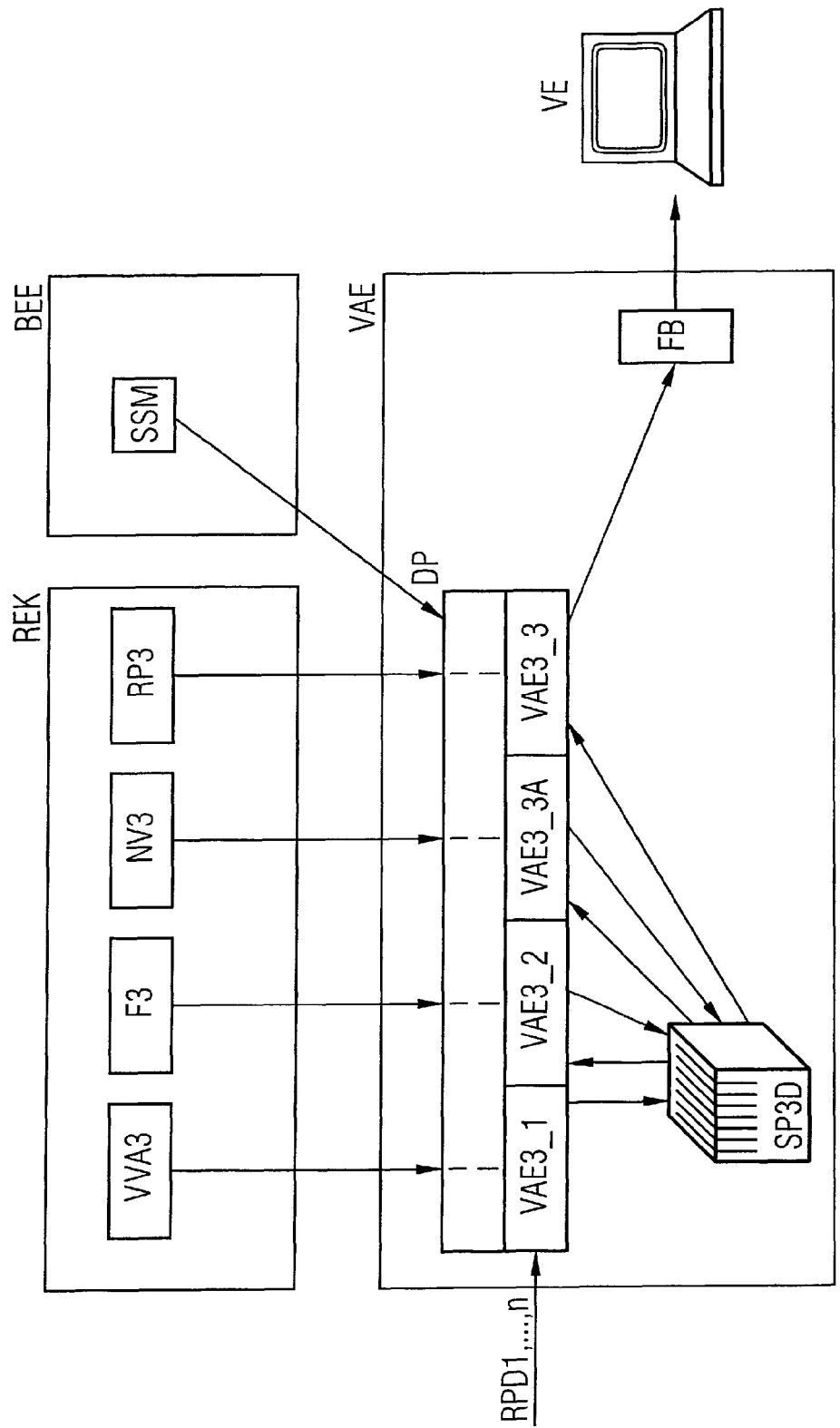
FIG. 2 is a block diagram of an embodiment of an image reconstruction and visualization procedure and apparatus in accordance with the present invention.

A block diagram according to an embodiment of the invention is shown in FIG. 2. Among other things, the reconstruction unit REK, an image generation unit BEE and a 2D/3D processing unit VAE are shown in this block diagram. Programs for a pre-processing VVA3, a filtering F3, a post-processing NV3 and a back-projection RP3 are stored in individual units VVA3, F3, NV3 and RP3 in the reconstruction unit REK. "Stored" means that these units have functional control of the tasks pre-processing, filtering, post-processing and back-projection and control their computational execution in the processing unit VAE. They are purely logical units, such that a function group for a projection matrix that is required for VVA3 and RP3 is present only once in REK. Programs, control data, look-up tables (LUTs) and projection matrices for the pre-processing are present in the pre-processing unit VVA3 and applied in VAE. In particular, the programs and projection matrices are also a rotation correction given circular tomography in the pre-stage for 3D filtering in the following unit F3. Programs, control data and filter seeds for a filtering or folding in 3D in virtual planes are held in the filter unit F3 and are applied in VAE. Programs and control data for the optimal image presentation in the visualization unit VE are held and applied in the post-processing unit NV3. Given the preceding complete reconstruction, NV3 ensues after the back-projection RP3. Otherwise, if partial results of RP3 should also be immediately visualized, it ensues before RP3. Given circular tomography, the rotation correction is calculated back again from VVA3. Programs, control data, projection matrices and look-up tables are stored in the back-projection unit RP3 for execution of the actual reconstruction in VAE3_3B. The generation and visualization of tomosynthesis volume images (for example) is implemented in a uniform approach with the embodiment of the processing unit VAE shown in FIG. 2 or 3. The processor-controlled raw image data processing implemented in the processing unit VAE ensues in multiple sub-modules VAE3_1, VAE3_2, VAE3_3A, VAE3_3B, VAE3_3, VAE3_4, VAE3_5. A value scaling, a physical correction, optionally a subtraction, an equalization, a rotation in the image plane and a projection correction ensue in the first sub-module VAE3_1 of the processing unit VAE. A filtering (convolution) for all projections in artificial planes within the 3D memory ensues in a second sub-module VAE3_2 of the processing unit VAE. The preferred preparation for the visualization in VE and possibly the reversal given non-linear (for example circular) tomosynthesis ensue in a third sub-modules VAE3_3A of the processing unit VAE. The precondition is that the generation of tomosynthesis slices and their visualization is implemented by the most customary method, the SSM method (slice stack method) in VAE only for the processing stages. Finally, the fourth sub-module VAE3_3B implements the reconstruction of the respective slice to be visualized from the entirety of the 3D data in SP3D_1 in real time. The data processor arranged in the processing unit VAE can address 2D and 3D data and arbitrarily process parallel image data in space, for example interpolate, rotate, shift, project, warp (distort) and fold.

The overlying blocks REK and BEE serve for illustration since, as shown in FIG. 1 and as is typical in the prior art, the reconstruction and the visualization are considered separate disciplines.

Pre-processing steps, filter tasks and a back-projection, and the presentation of the volume image data V according to specifications from REK and BEE, are executed by the data processor DP arranged in the 3D processing unit VAE.

The volume image data or the volume matrix V can be achieved, for example, by iterative algebraic methods ART: algebraic reconstruction technique or a filtered back-projection FPB. The data are thereby filtered and subsequently projected back onto the volume matrix V. The filtered back-projection FBP is thereby predominantly based on an analytical approach that is derived from the scan geometry. Iterative methods have particular importance given incomplete scan data.

For example, a direct 3D representation with the aid of a volume rendering method VR, a presentation similar to multiplanar reformatting MPR or a method for slice stack viewing SSM can be selected here as visualization algorithms according to specifications of the user. A film-like immersion in a slice stack in which one slice is shown after another is possible with the method for viewing the slice stack SSM since it corresponds in its volume views to the classical, film-based slice technique. VVA3 controls the importation (and thereby the pre-processing) of the raw projection data RPD1, . . . , RPDn. The processing unit VAE is supplied with corresponding programs, control data, projection matrices and look-up tables LUTs for this purpose.

VVA3 concerns the first module VAE3_1, the raw image data processing in the processing unit VAE. The module classification is, however, purely logically functional and to be viewed in the processing workflow as a structuring for better understanding of this workflow. Aside from this, VAE represents a unit for efficient 3D parallel processing.

The pre-processing is implemented in VAE3_1. A value scaling is conducted, for example with the aid of one or more LUTs. A detector-related physical correction can likewise be implemented. If necessary, subtraction or geometric equalization are implemented in the same sense of the pre-processing. Projection matrices can also be used, just as in an image rotation in the image plane concluding this stage or a very general projection correction. An entire plane prepared in a closed manner with raw image projection data RPDi can be stored in the 3D block memory SP3D_1 by the projection matrices or a complete projection matrix. "Closed" as used herein means that this preparation is conducted in a parallelized operation, and that the data represent a 3D unit. All of these partial functions can already ensue during the importation, i.e. on the path of the 2D raw projection data into the 3D memory block SP3D_1.

One step of a reconstruction-related filtering that can also be realized and designated as a folding is implemented with a filter algorithm associated with the module F3, with the aid of the processing unit VAE3_2. For this, in the 3D memory unit SP3D_1 a block of transformed RPD1 . . . RPDn, for example in a horizontal layer, is virtually redefined conceivably for the sequence of the processing but without restoring) in a slice layer perpendicular to this and such that the movement direction during the generation of the RPD acquisition series at least approximately represents a normal for the virtual slice. With such a folding, the filtering is implemented as a parallel offsetting of entire virtual planes relative to one another.

A post-processing program NV3 can subsequently be implemented in connection with the processing unit VAE3_3A which has already prepared the 3D data in the 3D memory SP3D_1 with regard to the visualization, for example scaled their values for corresponding optimal brightness and contrast, for example also using parallel addition of 3D planes and 3D columns to determine a value statistic as well as via look-up tables (LUTs). The adaptation of the values occurs in VAE3_3A and ensues with the use of memory within the 3D memory SP3D_1. In the case of a circular tomosynthesis, the rotation of the data planes back (which data planes were rotated in VVA3 for an improved filtering F3) is also conducted in VVAE3_3. The alignment (rotation) of the input for the second module VAE3_2 that is varied for the filtering given non-linear slice movement and existing as before for the third module VAE3_3, is reestablished without repeat processing effort in DP/VAE3_3A via the projection matrices.

The back-projection, implemented with the aid if the back-projection program RP3 in connection with the third/fourth module VAE3_3B/VAE3_3 (FIG. 2/FIG. 3) implements the reconstruction. Reconstruction and SSM rendering can be implemented together in real time in the module RP3 for the requirement of the generation of tomosynthesis views in classical slice orientation and the possibility of the dynamic immersion into the slice stack (SSM), which the DP implements in the (temporal) segment VAE3_3B. Every slice of the 3D volume to be visualized is generated at the moment in which it is desired for assessment. For this purpose, the fourth module VAE3_3B (FIG. 2) is supplied with projection matrices, look-up tables and coordinates from the reconstruction segment RP3 of the reconstruction unit REK. Based on these data and user-defined slice selection parameters from the module SMM of the image generation unit BEE, the last data processed by the third module VAE3_3A are offset (calibrated or matched) with one another relative to a slice of the SSM stack, and are stored in the frame buffer FB, the data therefrom being directly displayed on the monitor VE. The data from SP3D_1 are thereby again interpreted as planes parallel to the original RPD planes. The 3D volume generation is therefore realized for a slice stack in tomosynthesis on a parallel processing unit of the data processor DP with only one 3D memory SP3D_1 and with the consolidated volume generation and visualization. The reconstruction essentially consists of special processing (pre-post), filtering and back-projection. Back-projection and visualization (rendering) are implemented together in one pass using the plane-parallel offsetting of the data from the 3D memory SP3D_1.

Figure 3:
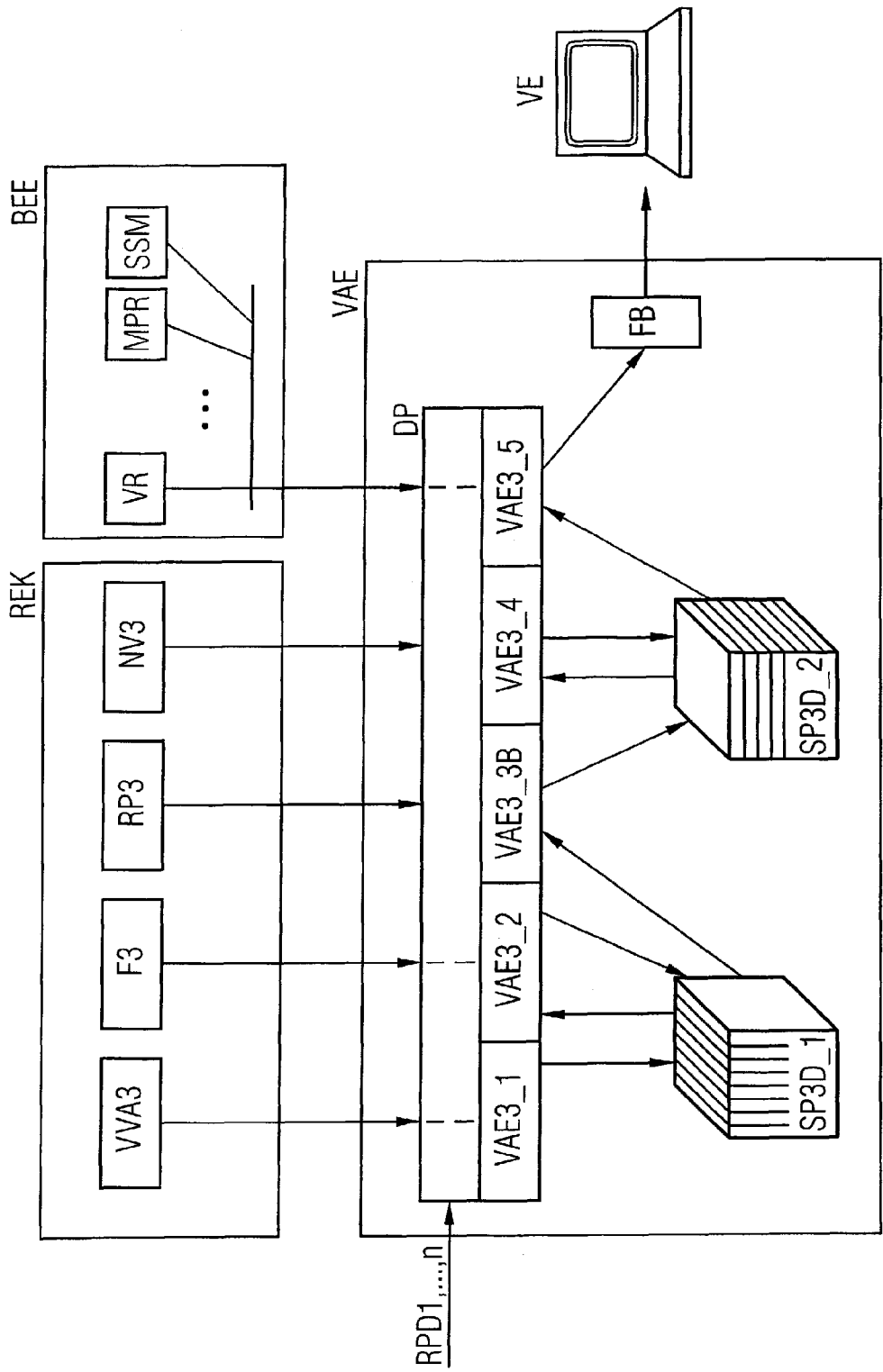
FIG. 3 illustrates further details of the embodiment of FIG. 2.

FIG. 3 represents a generalized realization in which the reconstruction is concluded in order to subsequently offer the full flexibility for different visualization methods, i.e. the selection possibility in BEE, for example between volume rendering VR, multiplanar reformatting MPR and slice stack method SSM.

The back-projection RP3 as an actual reconstruction task is concluded here in VAE3_3 and generates an arbitrarily visualizable 3D volume in SP3D_2. For this VAE3_3 is primarily supplied with projection matrices. With the use of these projection matrices, in connection with additional control data and coordinates the last (filtered) data processed by VAE3_2 are offset with one another, and volume data are therefore generated in SP3D_2. For this the input data in SP3D_1 are again interpreted as planes parallel to the original RPD planes. The alignment (rotation) that is possibly altered for the processing in VAE3_2 given non-linear slice movement is reestablished via the projection matrices without additional computational (processor) cost in the data processor DP in the unit VAE3_3.

The embodiment of the program in the module NV3 optionally allows a post-processing in place in connection with a second 3D memory SP3D_2 in the processing step in the fourth module VAE3_4 of the processing unit VAE. For example, a scaling for an optimal brightness and a contrast in the reproduction of the realization of determined characteristic line can be used in the fourth module VAE3_4. Look-up tables also are suitable for this procedure.

The 3D representation (visualization, rendering) is likewise implemented (and in principle in the same way) by the data processor DP. Depending on which presentation method was selected in the image generation unit BEE, the data from SP3D_2 are offset with one another in VAE3_5, i.e. projected in detail (for example again via projection matrices and with the aid of one or more look-up tables) and offset and output into the frame buffer FP whose content is presented 1:1 on the monitor as a 3D image. A real 3D impression can even be generated here with a stereo technique.

Figure 5:
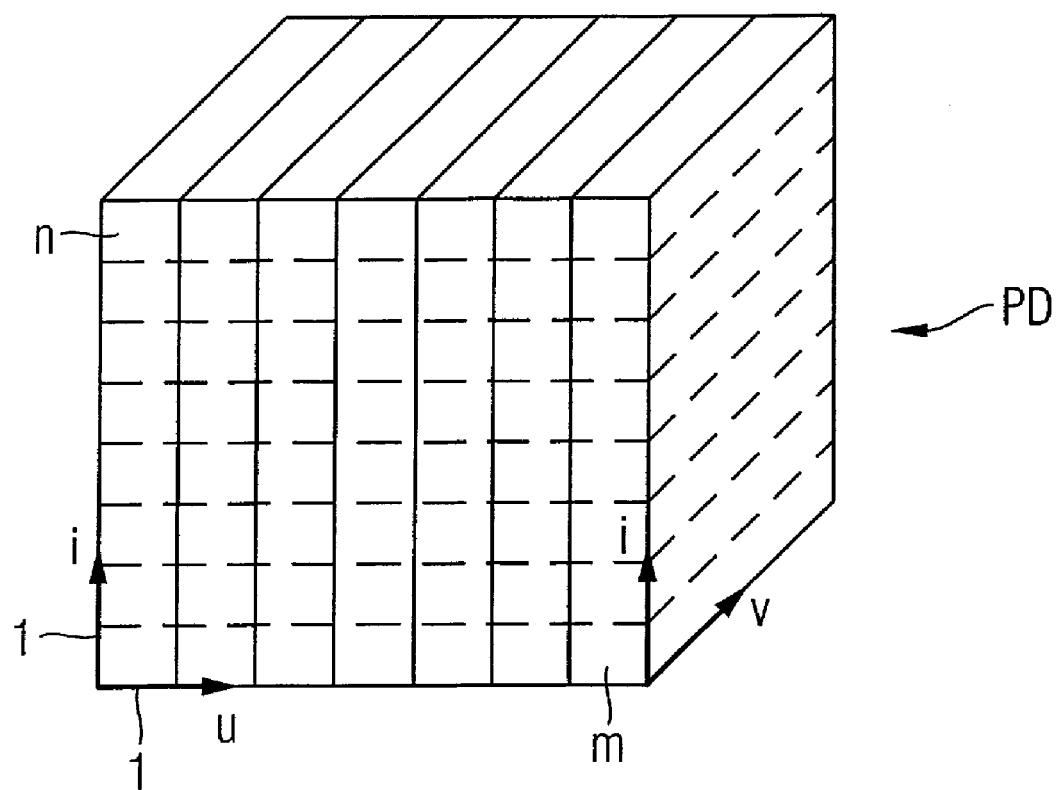
FIG. 5 schematically illustrates additional projection data for explaining the method according to the present invention.

In the second processing unit VAE3_2 downstream of the first module VAE3_1, the projection data PD stored in the 3D memory SP3D_1 are—as described in FIGS. 2, 3, 5—divided up into planes in (i, v)-alignment with normal vector i and are respectively processed in parallel slice-by-slice in one step. In an optional post-processing unit VAE3_3A positioned after the second module (the filter unit) VAE3_2, the values in the 3D memory SP3D_1 are post-processed in order to finally produce a good image control in the presentation. In the unit VAE3_3B/VAE3_3 following the filter unit VAE3_2 (or, respectively, following VAE3_3A if VAE3_3A is required), the reconstruction—thus the generation of the slices—is implemented with the known technique of back-projection, thus the generation of the slices. These slices are the actual result of the tomosynthesis. In the third module VAE3_3B/VAE3_3, the data in the 3D memory SP3D_1 are again interpreted parallel to the planes of the raw projection data RPD, thus in planes in (u,v)-alignment with normal vector i. The geometric correction in order to compensate for, for example, the rotation in the case of circular tomosynthesis is already implemented in the planes upon importation of the data in the third module VAE3_3B/VAE3_3 into the data pipeline. However, this is only a special case; arbitrary, general corrections as the acquisition conditions require are implemented with the concept of projection matrices. A designation of the slice to be reconstructed and displayed is communicated via the operation of the module for slice stack viewing SSM and the image generation unit BEE (rendering or visualization unit). This is implemented by the third module VAE3_3B. The data of all planes from the 3D memory SP3D_1 (thus the planes i with i=1. . . n) are matched and combined with one another and yield the respective current, visualized tomosynthesis slice in the frame buffer FB.

A general variant to acquire and present 3D tomosynthesis images is shown in FIG. 3 that possesses the advantage of optionally enabling different and continuative 3D representations. This variant is distinguished from the prior art in the same manner as the embodiment described in FIG. 2, through its closed, plane-parallel 3D processing in the data processor DP with the 3D memory block SP3D. In the third module VAE3_3, the reconstruction (thus the generation of the slices) is implemented with what is known as the technique of back-projection. These slices are the actual result of the tomosynthesis. In the third processing module VAE 3_3, the data in the 3D memory SP3D_1 are again interpreted parallel to the planes of the raw projection data RPD, thus in planes in (u,v)-alignment with normal vector u. As shown in FIG. 2, here as well the geometry is corrected with, for example, projection matrices in order to take into account laws in the acquisition or to cancel out modifications that were conducted for the more efficient pre-processing in the first module VAE3_1 and/or filtering in the second module VAE3_2. Depending on the resolution in the z-direction, a sufficiently large number n of slices that make the different visualization methods in the image generation unit BEE reasonable (for example the direct volume representation via volume rendering, VR) can be reconstructed depending on the acquisition parameters, for example a sufficiently large number of projections. Therefore it is advantageous to store the 3D volume calculated in the back-projection as such in a 3D block for which more and better visualization possibilities are available. The improvement of the 3D visualization even from an arbitrary viewing direction already begins here in a post-processing stage NV3 or, respectively, VAE3_4 downstream of the back-projection that optimally converts and adjusts the reconstructed values within the first region of the 3D memory (SP3D_1) for the presentation, for example with statistics about the total volume and by means of generation and application of look-up tables. In the fifth module VAE3_5 downstream of VAE3_4, the visualization ensues on the basis of the same 3D data in the second region of the 3D memory (SP3D_2) and with the same mechanisms as in the reconstruction. The data from the second 3D memory region SP3D_2 are converted for presentation and stored in the frame buffer FB in real time for every view. The conversion can include, for example, bringing arbitrarily slanted planes in SP3D_2 into registration by means of projection matrices as whole, projected plane regions and output of the result via one or more look-up table(s). Which type of visualization (VR, ... MPR, SSM) is employed is established by operation in the BEE, which leads to a corresponding parameterization of the VAE, specifically of the data processor DP in the phase VAE3_5.

Figure 4:
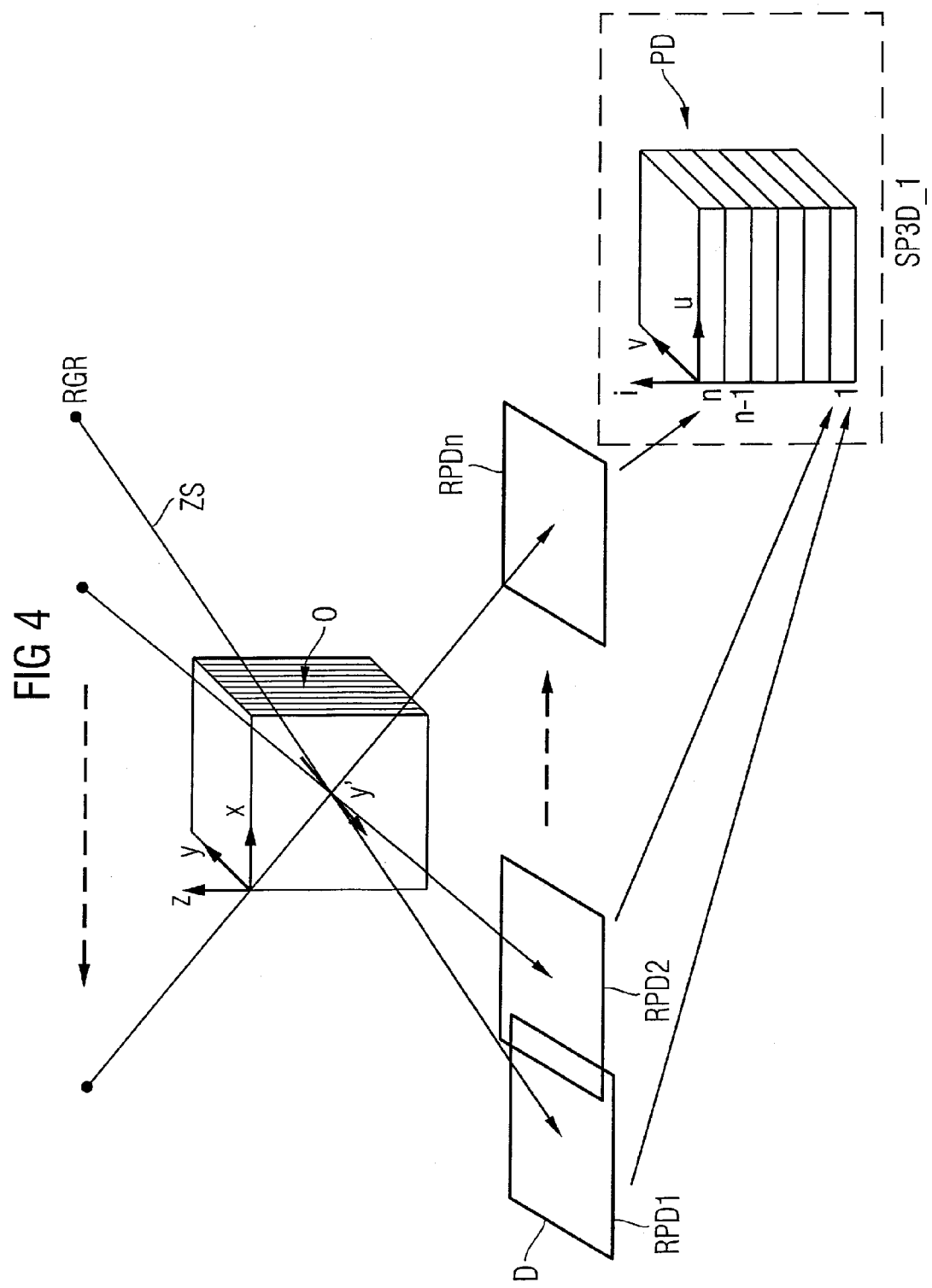
FIG. 4 schematically illustrates projection data for explaining the method according to the present invention.

FIG. 4 shows a schematic representation of how the raw projection data RPD1, ..., RPDn are generated and stored in the first 3D memory SP3D as projection data PD. Corresponding to the schematic representation, raw projection data RPD1, ..., RPDn of a subject O to be examined are created with an x-ray unit (not shown in detail) formed from a radiation source RGR and a detector unit D. The subject O is associated with a first coordinate system (x, y, z). During the examination, the raw projection data RPD associated with a second coordinate system (u, v) are associated with a second coordinate system (u, v, i) extended in the third dimension within the framework of the pre-processing. The x-ray source RGR is, for example, directed in the −x-direction in the first coordinate system beginning from the right and to the left. The raw projection data RPD1, ..., RPDn are stored by the detector D and are respectively retrieved by the processing unit VAE, controlled by the data processor. The raw image projections RPD1, ..., RPDn from the second coordinate system—for example the individual projections of a tomosynthesis exposure—are stored according to the second coordinate system, possibly are thereby already transformed and stored in the transformed form. The data are defined as a stack of 2D plane regions or as a 3D block that are stored in the first 3D memory SP3D_1. The image data or projection data PD of the individual projections are thereby stored per slice in the i-direction, corresponding to the second coordinate system u, v, i.

The projection exposures during the acquisition ensues in, for example, a movement parallel to the x-direction, and therefore also parallel to u; the primary required filter direction is thus parallel to u. Other slice images that were acquired in a series with direction not parallel to u are possible with advantageous additional processing if the stacking of the projections in the 3D texture block is adapted to the orientation of what is known as the slice figure, for example by a projection-dependent rotation of the data planes in the (u, v)-plane. This step does not need to be additionally canceled in the later back-projection since it can be formulated without additional computing effort as a modification of the projection matrices to be used.

A filter algorithm associated with the filter F3 can in the simplest case be a high-pass filter in the sense of a gradient filter or an unsharp masking or a one-dimensional folding of this nature with an arbitrary folding seed that, however, is implemented in parallel for complete (i,v)-plane regions. An exponential filtering described as an example in the DE 102006012407 can also be used here.

As shown in FIG. 5, the filtering of the projection data PD according to the invention ensues as, for example, what is known as 3D texture data in the i,v plane. The processor hardware of the data processor DP is fashioned for the filtering such that the texture data stored in 1 to n slices in the i-direction can be addressed not only as (u,v)-plane regions but rather as arbitrarily oriented plane regions, thus also as (i,v)-plane regions, and these arbitrarily oriented plane regions can be processed as entirely parallel; for example, a plane region u=1 can thus be completely offset with the plane region u=2 via the pipeline of the data processor DP. Every and multiple data planes can be included by the processor hardware in a processing step. Texture data of adjacent slices continuing in the u-direction can be taken into account with corresponding filter coefficients.

Depending on the type of reconstruction workflow, all calculations can ensue in place, or a second 3D storage space SP3D_2 is provided for the storage of the data in a second 3D data block.

An exemplary embodiment regarding a volume reconstruction V based on a raw image data acquisition is described in the following. For this these raw projection data are stored in a 2D/3D memory SP3D_1. The 2D textures (which can also be designated as projection image data) are stored in the planes 1 through n of the first 3D memory SP3D_1 in succession in increasing i-direction. Virtual new planes (for example (v,i)-planes) are subsequently defined for the reconstruction-related (pre-)filtering without having to resort to the 3D projection memory. It is only necessary to address SP3D_1, in a different manner, for example, in the form of addressing specific plane regions or textures. According to a selected filter algorithm, the data collected in (v,i)-plane regions with a respective specific u-coordinate are offset with one another as shown in FIG. 5. The parallel arithmetic logic unit of the 3D data processor that is specially designed for this is thereby used. Here it is, for example, a 2D parallel offsetting of entire (v,i)-plane regions with the goal of filtering all (u,v)-planes. For specific filter types (for example the unsharp masking) it can be advantageous that a second 3D data block of the same size and structure is used as a buffer that, however, is present anyway in the second 3D memory SP3D_2, and the filtering is not otherwise necessary in the phase. A filtering as described in DE 102006012407 can ensue entirely in place, i.e. without additional 3D memory requirement.

After the filtering, the filtered individual projections (as shown in FIGS. 2, 3, 4 and 6) are available in the first memory SP3D_1. For a tomosynthesis volume reconstruction, the (u,v)-planes are considered, for example as textures. Every covered region of the data planes from the i-stack is interpreted as a 3D texture; its acquisition geometry is correspondingly mapped and additively stored superimposed with the other mapped projections in a second reconstruction memory SP3D_2. The variable part of this acquisition geometry is determined by the acquisition angles of every projection, the position of the detector relative to the radiator and by the level of the slice that should presently be reconstructed. In the most general case, the geometry is described by a respective 3×4 projection matrix belonging to each projection.

For example, textures can be defined and handled as OpenGL QUADS. Whole texture surfaces can therefore be respectively calculated with the data processor DP with one call. In the case of the generation of classical slice images, a complete 3D reconstruction memory does not need to be provided since the reconstructed slices can be individually reconstructed and visualized in real time and/or can be stored in a storage medium, for example.

Taking into account the acquisition procedure in the tomosynthesis, the reconstruction-related filtering is subsequently begun immediately after the first x-ray acquisition or, respectively, the presence of the first raw projection data RPD1. This entails the advantage that the individual slices can be reconstructed and considered immediately after the end of the acquisition cycle. This makes sense for extremely complicated reconstruction-related filterings or simpler data processors. The previously described filtering (F3)/second module VAE3_2 is here integrated into the acquisition process as the pre-processing VVA3. This additionally entails the advantage that the data processor is better utilized and the time until viewing the slice images is additionally shortened. Since here only x-ray data of a projection plane are provided, filtering within the respective projection plane takes place parallel to the rows. This means that the x-ray image data of a v-row are offset in parallel with additional x-ray image data in the u-direction of the projection plane (u,v). The filtered projections are therefore ready for reconstruction in the first 3D memory SP3D_1 of the data processor DP immediately after the acquisition. For reconstruction, every projection is projected onto the memory plane [sic?] of every slice and is added there. This can be in the FB, or (given complete reconstruction) a plane with determined i in the second 3D memory SP3D_2. The complete reconstruction is a requirement if what are known as secondary reconstructions should be calculated, or if general 3D representations are desired, such as by means of volume rendering VR or multiplanar reformatting MPR. What is understood by a secondary reconstruction are views of the volume data set that do not run parallel to the planes of the slice process. Reconstruction and visualization in tomosynthesis can also be considered to belong together. Reconstruction and visualization can therefore ensue in pseudo-real time, at least given a standard slice consideration, and do not require a second 3D memory block but rather continuously generate new contents in the 2D frame buffer FB.

If pre-processing and filtering immediately before acquisition of a projections are concluded for this projection, and the result after filtering is stored in SP3D_1 (in the appertaining position i), the reconstruction can already be started during the next projection in that the data of the concluded projection are included in all voxels of the second 3D memory SP3D_2. The entire reconstruction is thus concluded immediately after acquisition of the last projection and its inclusion in the second 3D memory SP3D_2. SP3D_1 is therefore limited to memory space for two projection data planes, the currently acquired data plane and the finished, filtered data plane that is directly included in the reconstruction.

So that the assessor can make the correct location selection, an orientation image (comparable to a topogram in computer tomography) can be created. This can, for example, be a lateral or axial image given coronal slice direction. Since, after filtering and reconstruction, the complete volume data set is ready in the reconstruction memory of the second 3D memory unit SP3D_2 of the data processor DP, the visualization of an orientation image is possible, for example via summation of planes in real time.

As shown in FIG. 4, a series of raw x-ray projections is created in a tomosynthesis acquisition system with a configuration in which the central ray can rotate around an axis, wherein the focus advantageously but not necessarily moves linearly or, respectively, parallel to an axis on the one side of the acquisition subject. The detector D likewise advantageously moves linearly with the central ray ZS on the other side of the subject O. The detector D can also be decoupled from the x-ray source. In this case, the detector could rest if it is large enough to image all projections of the subject O.

In the further consideration, a mammography apparatus is assumed in which the x-ray tube describes a circular arc while the detector is arranged stationary at the mammography apparatus. In one acquisition as shown in FIG. 4, a series of raw projection images that correspond slice for slice $(u,v)_i$ to a projection stack are loaded as projection data PD into the first memory SP3D_1 of the data processor DP. The pre-processing subsequently essentially ensues with geometric and value-based scaling. The reconstruction-related (pre-) filtering follows according to a recursive method approximating Shepp and Logan core for preparation of the pure reconstruction that, in this case, is realized as a back-projection.

In order to be able to optimally use the pipeline of the data processor DP, the stored projection slices as shown in FIG. 4 are treated for the filtering as (v,i)-textures and offset from one another. This is equivalent to a parallel filtering for all point series or point columns in the u-direction. For example, the operation of the OpenGL alpha blending can be directly used here for the recursive, possibly exponential calculation here. Given specific multiple filterings, for example the combination of linear low-pass filters with subtraction for the purpose of an unsharp masking, it can be necessary to apply a second texture block of the same dimensions in the second 3D memory SP3D_2. The intermediate results of the odd processing steps are stored in this second 3D memory SP3D_2. The direct processing steps ensue back in the first block. The data for the actual back-projection are available after this reconstruction-related filtering.

Figure 6:
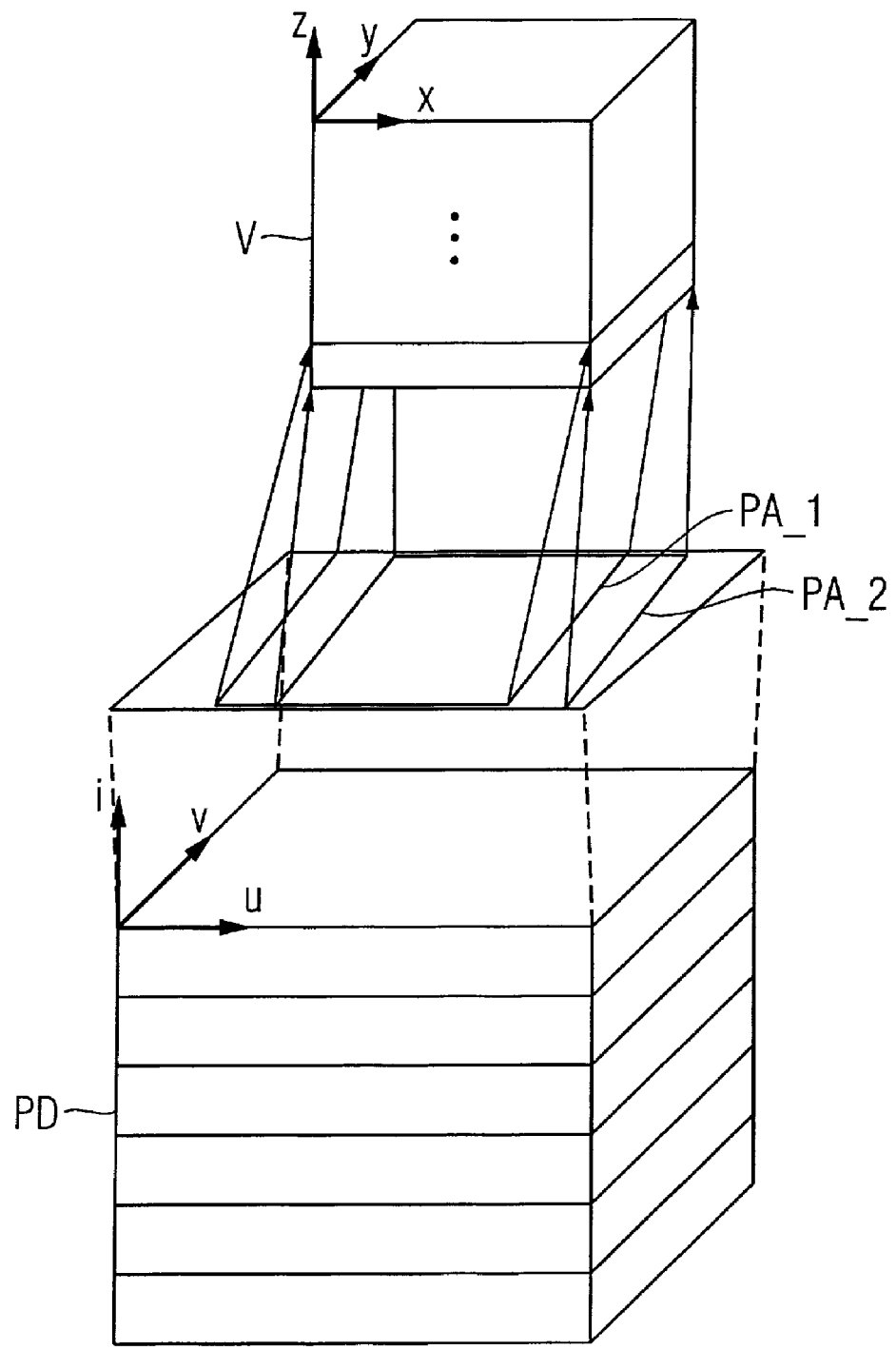
FIG. 6 schematically illustrates reconstruction data for explaining the method according to the present invention.

As indicated in FIG. 6, a limited memory range for a 3D memory stack or, respectively, 3D memory block as a second 3D memory region SP3D_2 is advantageously set up for the entire reconstruction volume V. Given storage of all reconstructed data in the second 3D memory SP3D_2, the volume can be visualized in different ways in different perspectives.

Figure 7:
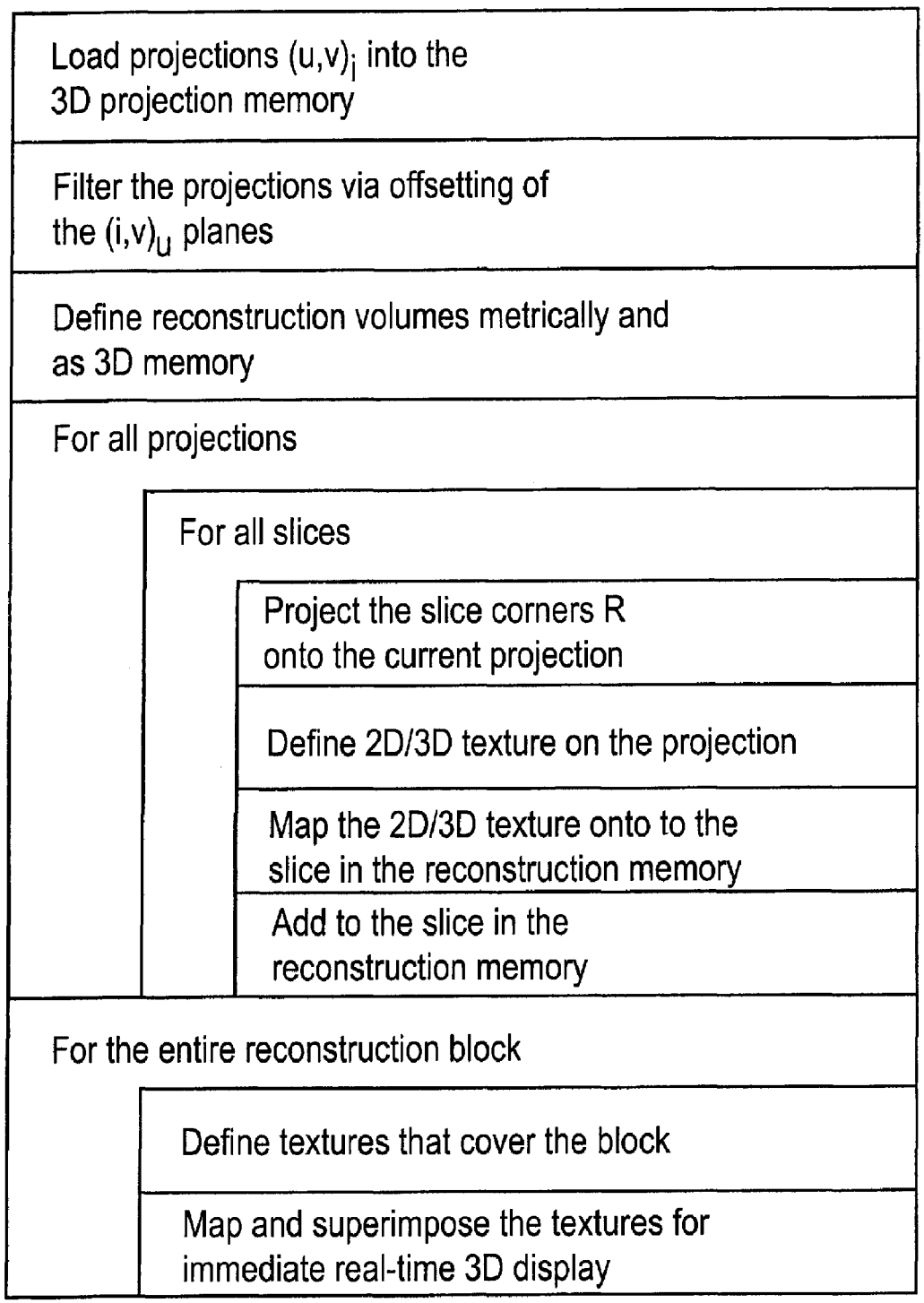
FIG. 7 is a block diagram of a further embodiment of the method and apparatus according to the present invention.
Figure 8:
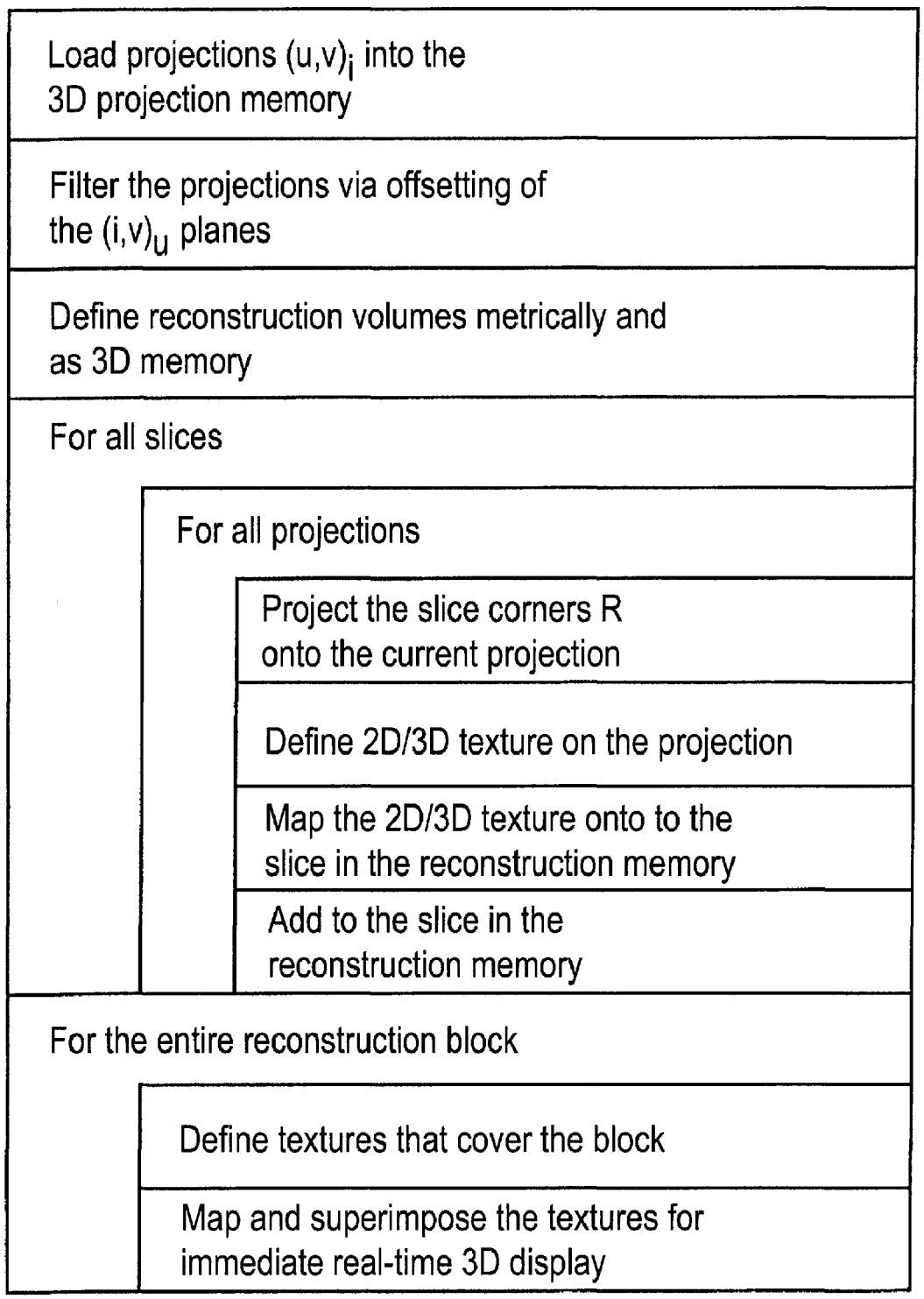
FIG. 8 shows further details of the embodiment of FIG. 7.

In the reconstruction of the volume V, a projection plane is respectively picked out of the filtered projection data PD in SP3D_1 and included in the second memory SP3D_2. For example, the plane region from the last projection (uppermost of n filtered projections in the stack in the first 3D memory SP3D_1) is designated with the first projection portion PA_1, which represents a contribution to the lowermost slice in the reconstruction volume V; the plane region from the same last projection which represents a contribution to the second lowermost slice in the reconstruction volume V is designated with the second projection portion PA_2. In the reconstruction (back-projection), the possibility is offered to execute a loop across the projections, or a loop across the reconstructed slices, as an outermost loop. If the loop is on the outside across the projections, data inside the memory block accumulate into the complete reconstruction stack. If the external loop runs over the reconstruction volume, every slice of the reconstruction volume is completely calculated from all projections and can then be visualized and stored away, such that here a 3D memory block does not need to be completely provided for the reconstructed slices. In every variant, a projection of a reconstruction volume slice is mapped in the innermost loop. As is listed in the workflow diagram in FIG. 7, 9, this can occur as indicated according to the following, in particular in FIG. 6. The four corners $(x,y,z)_{1-4}$ of the present slice z to be reconstructed on the respective projection i are mapped to four points $(u,v)_{1-4}$ on the detector according to the following rule: a point (u,v) on the detector D that belongs to a volume point (x,y,z) is calculated as $$v_d=(r,s,t)'=M_i*v_v$$

$$u=r/t;$$

$$v=s/t$$

with $M_i$: 3x4 projection matrix in homogeneous coordinates for projection i $v_d$: column vector in detector coordinates (r,s,t)

$V_v$: column vector in homogeneous volume coordinates (x,y,z,1)

The 4 points $(u,v)_{1-4}$ define a (not necessarily) rectangular texture from the projection memory PD that is mapped or, respectively, warped to a rectangular 2D xy-reconstruction volume slice. This should mean: areal interpolation and accumulation in the 2D xy-memory. A decisive performance gain results via this areal parallel processing with which the entire 3D volume is covered. The entire (pre-)filtering with exponential seed is possible in a few ms in the pipeline of the data processor DP, which requires a multiple of the reconstruction time in a conventional, sequential realization. The filtering can also be implemented within every projection, thus every (u,v)-plane. The calculations for filtering and reconstruction can therefore be started immediately after the acquisition of the first projection and are finished approximately simultaneously with the acquisition. The proposed method thus enables real-time tomosynthesis without wait time, most of all because the tomosynthesis reconstruction can be hidden after the visualization. The complete reconstruction in the graphical arithmetic logic unit additionally also primarily has the advantage that the volume V is already loaded for a direct visualization. 2D or 3D texture mapping can be re-used for this visualization, so to speak in the reverse direction, i.e. as a projection of volume onto a plane (for example a monitor screen), and video frame rates are achieved in real time.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for tomosynthesis reconstruction and visualization of projection data, comprising:
    a computerized data processor comprising a raw data processing unit, a reconstruction unit, and an image data processing unit;
    said data processor comprising an input port supplied with raw 2D projection data, for a plurality of 2D projection, obtained from a detector unit of an x-ray imaging apparatus;
    said raw data processing unit being configured to load at least one module in said raw data processing unit with said raw 2D projection data as a 3D data block, said at least one module comprising data processing programs, including a 3D tomosynthesis image reconstruction program, and parameters stored in said reconstruction unit and said image data processing unit;
    said module in said raw data processing unit being configured to process the raw 2D projection data in parallel in said 3D data block by simultaneously filtering all of said 2D projections in said 3D data block in parallel, to obtain processed and filtered data;
    said at least one module also being configured to reconstruct a tomosynthesis image from the processed said 3D tomosynthesis image reconstruction program and filtered data, according to and said parameters stored in the reconstruction unit; and
    said module also being configured to cause a 3D volume rendering of the reconstructed tomosynthesis image to be displayed, according to programs and parameters stored in said image generation unit, said 3D volume rendering being comprised of individual slices, and said module being configured to make data for displaying at least some of said slices available before completion of an entirety of the reconstruction of said tomosynthesis image.

2. An apparatus as claimed in claim 1 wherein said module is configured to implement a rotation of the raw projection data.

3. An apparatus as claimed in claim 1 wherein said module is a first module, and wherein said data processor comprises a second module loaded with programs from said image processing unit that cause projection data stored along an I-axis in the u-v-direction of a coordinate system to be assembled within arbitrary slice planes in the coordinate system to implement a computerized filtering process that is implemented n times, with said slice planes being subjected to said filtering in parallel.

4. An apparatus as claimed in claim 1 wherein said module is a first module and wherein said data processor comprises a second module loaded with programs from said image processing unit to process projection data respectively representing at least two slice planes extending in the u-v-direction of a coordinate system, said raw projection data being stored in n u-v-parallel planes in said coordinate system, and being subjected to computerized filtering in parallel n times.

5. An apparatus as claimed in claim 1 wherein said module is a first module and wherein said data processor comprises a second module loaded with programs from said image processing unit, wherein projection data are stored in n u-v-parallel planes of a coordinate system and are assembled within n v-i slice planes in said coordinate system in a filtering process implemented n times, with projection data for at least two v-i slice planes being filtered in parallel.

6. An apparatus as claimed in claim 1 comprising a back-projection module controlled by a back-projection unit in said image processing unit to implement a back-projection of complete u-v planes of filtered 2D projection data in a reconstruction volume using 2D or 3D texture mapping with a parallel accumulation of mapped data in processed regions of the reconstruction volume.

7. An apparatus as claimed in claim 1 comprising a filter module controlled by a filter unit for filtering raw projection data on a slice-by-slice basis by processing the data in parallel line-by-line during the acquisition of the raw projection data for at least one slice, said filtering being executed n times.

8. A method for reconstruction and visualization of projection data, comprising the steps of:
    configuring a computerized data processor to include a raw data processing unit, a reconstruction unit, and an image data processing unit;
    supplying said data processor with raw 2D projection data, for a plurality of 2D projections obtained from a detector unit of an x-ray imaging apparatus, to said processor;
    in said raw data processing unit, loading at least one module in said raw data processing unit with said raw 2D projection data as a 3D data block, said at least one module comprising data processing programs, including 3D tomosynthesis image reconstruction program, and parameters stored in said reconstruction unit and said image data processing unit;
    processing the raw 2D projection data in said module in said raw data processing unit in parallel in said 3D data block by simultaneously filtering all of said 2D projections in said 3D data block in parallel, to obtain processed and filtered data;

also in said at least one module, reconstructing a tomosynthesis image from the processed and filtered data, according to said 3D tomosynthesis reconstruction program and said parameters stored in the reconstruction unit; and said module also causing a 3D volume rendering of the reconstructed tomosynthesis image to be displayed, according to programs and parameters stored in said image generation unit, said 3D volume rendering being comprised of individual slices, and said module making data for displaying at least some of said slices available before completion of an entirety of the reconstruction of said tomosynthesis image.

9. A method as claimed in claim 8 comprising in said module implementing a rotation of the raw projection data.

10. A method as claimed in claim 8 wherein said module is a first module, and comprising loading a second module in said data processor comprises with programs from said image processing unit that cause projection data stored along an I-axis in the u-v-direction of a coordinate system to be assembled within arbitrary slice planes in the coordinate system to implement a computerized filtering process that is implemented n times, with said slice planes being subjected to said filtering in parallel.

11. A method as claimed in claim 8 wherein said module is a first module and comprising loading a second module in said data processor with programs from said image processing unit to process projection data respectively representing at least two slice planes extending in the u-v-direction of a coordinate system, said raw projection data being stored in n u-v-parallel planes in said coordinate system, and being subjected to computerized filtering in parallel n times.

12. A method as claimed in claim 8 wherein said module is a first module and comprising loading a second module loaded in said data processor with programs from said image processing unit, wherein projection data are stored in n u-v-parallel planes of a coordinate system and are assembled within n v-i slice planes in said coordinate system in a filtering process implemented n times, with projection data for at least two v-i slice planes being filtered in parallel.

13. A method as claimed in claim 8 comprising, in a back-projection module controlled by a back-projection unit in said image processing unit implementing a back-projection of complete u-v planes of filtered 2D projection data in a reconstruction volume using 2D or 3D texture mapping with a parallel accumulation of mapped data in processed regions of the reconstruction volume.

14. A method as claimed in claim 8 comprising, in a filter module controlled by a filter unit, filtering raw projection data on a slice-by-slice basis by processing the data in parallel line-by-line during the acquisition of the raw projection data for at least one slice, said filtering being executed n times.

* * * * *